(12) United States Patent
Summitt et al.

(10) Patent No.: US 12,232,722 B2
(45) Date of Patent: Feb. 25, 2025

(54) COINED SUTURE PASSING DRILL

(71) Applicant: Conmed Corporation, Utica, NY (US)

(72) Inventors: Matthew Summitt, Palm Harbor, FL (US); Robert A. Thibodeau, Saint Petersburg, FL (US)

(73) Assignee: Conmed Corporation, Utica, NY (US)

( * ) Notice: Subject to any disclaimer, the term of this patent is extended or adjusted under 35 U.S.C. 154(b) by 14 days.

(21) Appl. No.: 17/052,998

(22) PCT Filed: May 7, 2019

(86) PCT No.: PCT/US2019/030995
§ 371 (c)(1),
(2) Date: Nov. 4, 2020

(87) PCT Pub. No.: WO2019/217345
PCT Pub. Date: Nov. 14, 2019

(65) Prior Publication Data
US 2021/0068815 A1      Mar. 11, 2021

Related U.S. Application Data

(60) Provisional application No. 62/668,900, filed on May 9, 2018.

(51) Int. Cl.
*A61B 17/04* (2006.01)
*A61B 17/16* (2006.01)

(52) U.S. Cl.
CPC ...... *A61B 17/0485* (2013.01); *A61B 17/0401* (2013.01); *A61B 17/1615* (2013.01);
(Continued)

(58) Field of Classification Search
CPC ............ A61B 17/0401; A61B 17/0485; A61B 17/1615; A61B 17/1631; A61B 17/1682;
(Continued)

(56) References Cited

U.S. PATENT DOCUMENTS 4,182,341 A    1/1980  Perri
4,345,899 A *  8/1982  Vlock ..................... A61C 3/02
                                                    433/165
(Continued)

FOREIGN PATENT DOCUMENTS

EP    2198795         6/2010
EP    2198795 A1      6/2010
WO    2006/009471     1/2006

OTHER PUBLICATIONS

JP Office Action, App. No. 2020-562116, dated Sep. 28, 2021, pp. 1-13.
(Continued)

*Primary Examiner* — Diane D Yabut
*Assistant Examiner* — C. D. K.
(74) *Attorney, Agent, or Firm* — Bond, Schoeneck & King, PLLC; Frederick J. M. Price

(57) ABSTRACT

A suture passing drill for passing suture through bone. The suture passing drill includes a proximal end and a distal end with an elongated shaft extending therebetween. The elongated shaft has first portion with a first diameter. The drill also includes a wire loop extending from the proximal end of the elongated shaft and a drill tip at the distal end of the elongated shaft. The elongated shaft has a narrow portion with a second diameter, which is smaller than the first diameter. The narrow portion is positioned proximally adjacent relative to the drill tip. The narrow portion is preferably created through coining. Coining prevents the need for machining the outer diameter (or surface) of the elongated shaft proximal to the drill tip in order to create a larger drill tip. The larger drill tip of the suture passing drill allows for passage of the entire drill through the bone hole.

20 Claims, 9 Drawing Sheets

(52) U.S. Cl.
CPC .. *A61B 17/1631* (2013.01); *A61B 2017/0404* (2013.01); *A61B 2017/0409* (2013.01); *A61B 2017/0496* (2013.01)

(58) Field of Classification Search
CPC ........ A61B 17/1697; A61B 2017/0404; A61B 2017/0409; A61B 17/0482; A61B 17/06004; A61B 17/06066; D05B 85/00; D05B 85/003; D05B 85/006; D05B 85/02; D05B 85/04; D05B 85/06; D05B 85/08; D05B 85/10; D05B 85/12; D05B 85/14; D05B 87/00; D05B 87/02; D05B 87/04

See application file for complete search history.

(56) References Cited

U.S. PATENT DOCUMENTS

| | | | |
|---|---|---|---|
| 4,373,518 A * | 2/1983 | Kaiser | A61B 17/1615 606/329 |
| 4,990,088 A * | 2/1991 | Weissman | A61C 3/02 433/102 |
| 5,055,105 A * | 10/1991 | Hamlin | A61B 17/1615 606/80 |
| 5,257,996 A * | 11/1993 | McGuire | B25G 1/043 606/104 |
| 5,788,699 A * | 8/1998 | Bobst | A61B 17/1615 408/229 |
| 6,045,551 A | 4/2000 | Bonutti | |
| 6,117,160 A | 9/2000 | Bonutti | |
| 6,132,433 A * | 10/2000 | Whelan | A61F 2/0811 623/13.12 |
| 6,638,279 B2 | 10/2003 | Bonutti | |
| 6,991,636 B2 | 1/2006 | Rose | |
| 7,066,956 B2 | 6/2006 | Schmieding et al. | |
| 7,077,863 B2 | 7/2006 | Schmieding et al. | |
| 7,235,091 B2 | 6/2007 | Thornes | |
| 7,306,626 B2 | 12/2007 | Whelan | |
| 7,481,825 B2 | 1/2009 | Bonutti | |
| 7,588,595 B2 | 9/2009 | Miller et al. | |
| 7,713,300 B2 | 5/2010 | Meridew et al. | |
| 7,905,903 B2 | 3/2011 | Stone et al. | |
| 7,905,904 B2 | 3/2011 | Stone et al. | |
| 7,988,697 B2 | 8/2011 | Miller et al. | |
| 8,298,262 B2 | 10/2012 | Stone et al. | |
| 8,398,678 B2 | 3/2013 | Baker et al. | |
| 8,409,225 B2 | 4/2013 | Bull et al. | |
| 8,425,554 B2 | 4/2013 | Denove et al. | |
| 8,449,552 B2 | 5/2013 | Sanders | |
| 8,500,809 B2 | 8/2013 | Saliman et al. | |
| 8,506,597 B2 | 8/2013 | Kaiser et al. | |
| 8,512,375 B2 | 8/2013 | Torrie et al. | |
| 8,512,376 B2 | 8/2013 | Thornes | |
| 8,562,647 B2 | 10/2013 | Kaiser et al. | |
| 8,579,553 B2 | 11/2013 | Pierce | |
| 8,621,961 B2 | 1/2014 | Burch et al. | |
| 8,734,491 B2 | 5/2014 | Seavey | |
| 8,888,795 B2 | 11/2014 | Chu | |
| 8,888,815 B2 | 11/2014 | Holmes, Jr. | |
| 8,888,848 B2 | 11/2014 | Saliman et al. | |
| 8,961,575 B2 | 2/2015 | Choinski | |
| 9,005,245 B2 | 4/2015 | Thornes et al. | |
| 9,005,287 B2 | 4/2015 | Stone | |
| 9,072,510 B2 | 7/2015 | Thornes et al. | |
| 9,138,223 B2 | 9/2015 | Jolly et al. | |
| 9,173,652 B2 | 11/2015 | Lombardo et al. | |
| 9,204,874 B2 | 12/2015 | Denove et al. | |
| 9,320,512 B2 | 4/2016 | Dooney, Jr. | |
| 9,402,621 B2 | 8/2016 | Stone et al. | |
| 9,421,008 B2 | 8/2016 | Burkhart et al. | |
| 9,445,803 B2 | 9/2016 | Marchand et al. | |
| 9,463,011 B2 | 10/2016 | Dreyfuss et al. | |
| 9,468,433 B2 | 10/2016 | Denham et al. | |
| 9,538,998 B2 | 1/2017 | Stone et al. | |
| 9,561,025 B2 | 2/2017 | Stone et al. | |
| 9,642,609 B2 | 5/2017 | Holmes, Jr. | |
| 9,700,291 B2 | 7/2017 | Norton et al. | |
| 9,795,398 B2 | 10/2017 | Steiner et al. | |
| 9,800,027 B1 | 10/2017 | Pierce | |
| 9,826,971 B2 | 11/2017 | Lombardo et al. | |
| 9,848,868 B2 | 12/2017 | Saliman | |
| 9,913,638 B2 | 3/2018 | Saliman et al. | |
| 9,918,711 B2 | 3/2018 | Seavey | |
| 9,918,826 B2 | 3/2018 | Berelsman et al. | |
| 9,962,150 B2 | 5/2018 | Rodriguez et al. | |
| 9,974,534 B2 | 5/2018 | Troxel et al. | |
| 10,143,469 B2 | 12/2018 | Denove et al. | |
| 10,206,670 B2 | 2/2019 | Thornes | |
| 10,251,637 B2 | 4/2019 | Stone et al. | |
| 10,299,802 B2 | 5/2019 | Saylor et al. | |
| 10,321,906 B2 | 6/2019 | Stone et al. | |
| 10,390,816 B2 | 8/2019 | Thornes | |
| 10,448,942 B2 | 10/2019 | Santangelo et al. | |
| 10,448,944 B2 | 10/2019 | Marchand et al. | |
| 10,687,798 B2 | 6/2020 | Lombardo et al. | |
| 10,695,045 B2 | 6/2020 | Kaiser et al. | |
| 10,702,259 B2 | 7/2020 | Stone et al. | |
| 10,736,620 B2 | 8/2020 | Dreyfuss et al. | |
| 10,758,221 B2 | 9/2020 | Berelsman et al. | |
| 2004/0243135 A1 | 12/2004 | Koseki | |
| 2007/0276395 A1 | 11/2007 | Burn | |
| 2009/0171360 A1 | 7/2009 | Whelan | |
| 2010/0152752 A1 * | 6/2010 | Denove | A61B 17/06109 606/228 |
| 2010/0217315 A1 * | 8/2010 | Jolly | A61B 17/06 606/223 |
| 2011/0087248 A1 | 4/2011 | Steffen | |
| 2011/0238071 A1 | 9/2011 | Fernandez-Scoma | |
| 2012/0003057 A1 | 1/2012 | Leyba | |
| 2012/0016428 A1 | 1/2012 | White et al. | |
| 2012/0071878 A1 | 3/2012 | Cowin | |
| 2012/0197395 A1 | 8/2012 | Berg | |
| 2012/0197396 A1 | 8/2012 | Berg | |
| 2013/0090658 A1 | 4/2013 | Kam | |
| 2013/0138150 A1 | 5/2013 | Baker et al. | |
| 2013/0218273 A1 | 8/2013 | Bull et al. | |
| 2013/0331886 A1 | 12/2013 | Thornes | |
| 2014/0243893 A1 * | 8/2014 | Santangelo | A61B 17/0401 606/232 |
| 2014/0330307 A1 | 11/2014 | Steffen | |
| 2018/0049734 A1 | 2/2018 | Kam | |
| 2018/0049775 A1 | 2/2018 | Krause | |

OTHER PUBLICATIONS

International Search Report Form PCT/ISA/220, International Application No. PCT/US2019/030995, pp. 1-14, Dated Aug. 22, 2019.
Korean Final Office Action, Application No. 10-2020-7034554, dated Mar. 10, 2023, pp. 1-3.
Translated Chinese First Office Action, App. No. 201980036962.3, dated Nov. 28, 2023, Nov. 28, 2023, pp. 1-16.

* cited by examiner

COINED SUTURE PASSING DRILL

CROSS-REFERENCES TO RELATED APPLICATIONS

This application is a national stage application under 35 U.S.C. 371 based on international patent application PCT/US19/30995 filed on May 7, 2019, which claims priority to U.S. Provisional Patent Application Ser. No. 62/668,900, filed on May 9, 2018, the entireties of which are incorporated herein by reference.

BACKGROUND OF THE INVENTION

1. Field of the Invention

The present invention is directed generally to a surgical drill and, more particularly, to a drill for passing suture through bone.

2. Description of Related Art

Surgical procedures that require the repair of torn or damaged soft tissue are fairly common. Similarly, many orthopedic surgeries require suspension created between two bodies, such as between two bones or between soft tissue and bone. The purpose of the suspension is to hold the first body in a desirable location relative to the second body. In one exemplary orthopedic procedure, a plantar plate repair, a torn or otherwise damaged ligament in the foot is re-approximated to a bone in the toe. This procedure is typically done by drilling two holes in the bone, pulling one limb of suture through each hole, and tying a knot in each limb outside each bone hole.

According to the traditional method for plantar plate repair, two bone holes must be drilled through the bone in order to create a bone bridge for tying off the suture and creating the required suspension between the torn tissue and the bone. However, in orthopedic procedures, drilling two bone holes creates at least twice as much trauma at the surgical repair site. The trauma created by the bone holes is exacerbated in surgical procedures such as the plantar plate repair where the bone is a relatively small bone in the extremities. In such situations where the surgical repair site is located in an extremity, drilling two bone holes can cause an intolerable amount of damage to the bones. In addition, in some instances, it is not possible to drill two holes due to the limited space on the small bones.

In another exemplary procedure, a trapeziectomy for thumb arthritis requires suspension of the CMC joint between the carpal (i.e. wrist bone) and the metacarpal (i.e. proximal thumb bone). Currently, the suspension of the CMC joint is performed by first, drilling a tunnel between the carpal and metacarpal, and then, using a pair of metal buttons with suture tied in between. However, the drills used to create the bone tunnel have a drill tip or bit that is the same size or smaller than the remainder of the drill.

Therefore, there is a need for a drill with a larger tip for creating a large bone tunnel for passing the remainder of the drill.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a suture passing drill that is optimal for passing suture through bone. According to one aspect, the suture passing drill includes a proximal end and a distal end with an elongated shaft extending therebetween. A first portion of the elongated shaft has a first diameter. The drill also includes a wire loop extending from the proximal end of the elongated shaft and a drill tip at the distal end of the elongated shaft. The elongated shaft has a narrow portion with a second diameter, which is smaller than the first diameter. The narrow portion is proximally adjacent relative to the drill tip and distally adjacent to the portion of the elongated shaft with the first diameter. Alternatively, the narrow portion can be positioned between two portions of the elongated shaft with the first diameter, or at the very proximal end of the elongated shaft with a portion of the elongated shaft with the first diameter immediately proximately adjacent thereto.

According to another aspect, the present invention is a method for tensioning a first body relative to a second body. The method includes the steps of: (i) providing a suture passing drill comprising a proximal end and a distal end with an elongated shaft extending therebetween, the elongated shaft having a first portion with a first diameter, a wire loop extending from the proximal end of the elongated shaft, a drill tip at the distal end of the elongated shaft, a narrow portion on the elongated shaft having a second diameter, the narrow portion being proximally adjacent relative to the drill tip, wherein the second diameter is smaller than the first diameter; (ii) attaching a length of suture to the wire loop; (iii) drilling a first hole in a first body with the drill tip of the suture passing drill; (iv) drilling a second hole in a second body with the drill tip of the suture passing drill; and (v) pulling the suture passing drill through the second hole such that the length of suture extends between the first body and the second body.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1A:
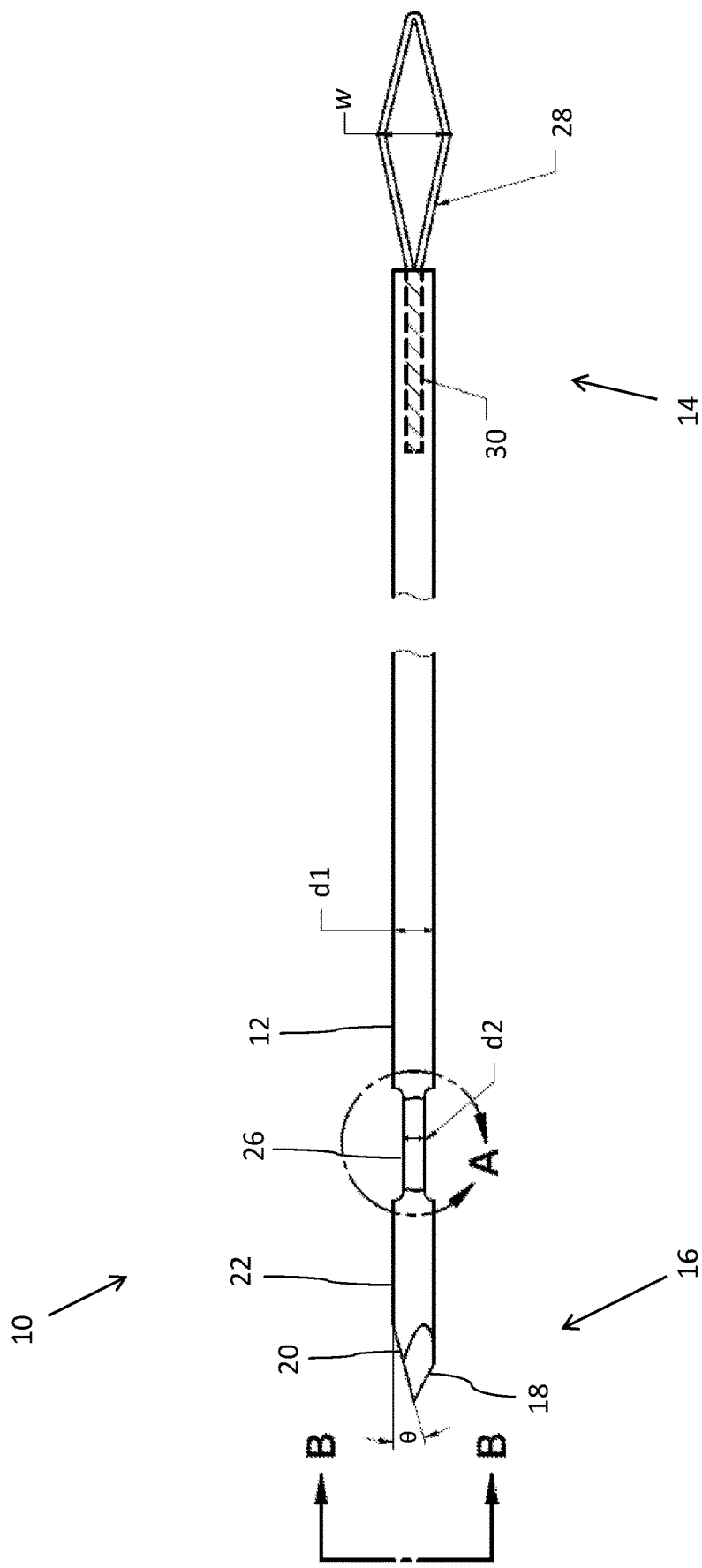
FIG. 1A is a side view schematic representation of a suture passing drill, according to an embodiment.
Figure 1B:
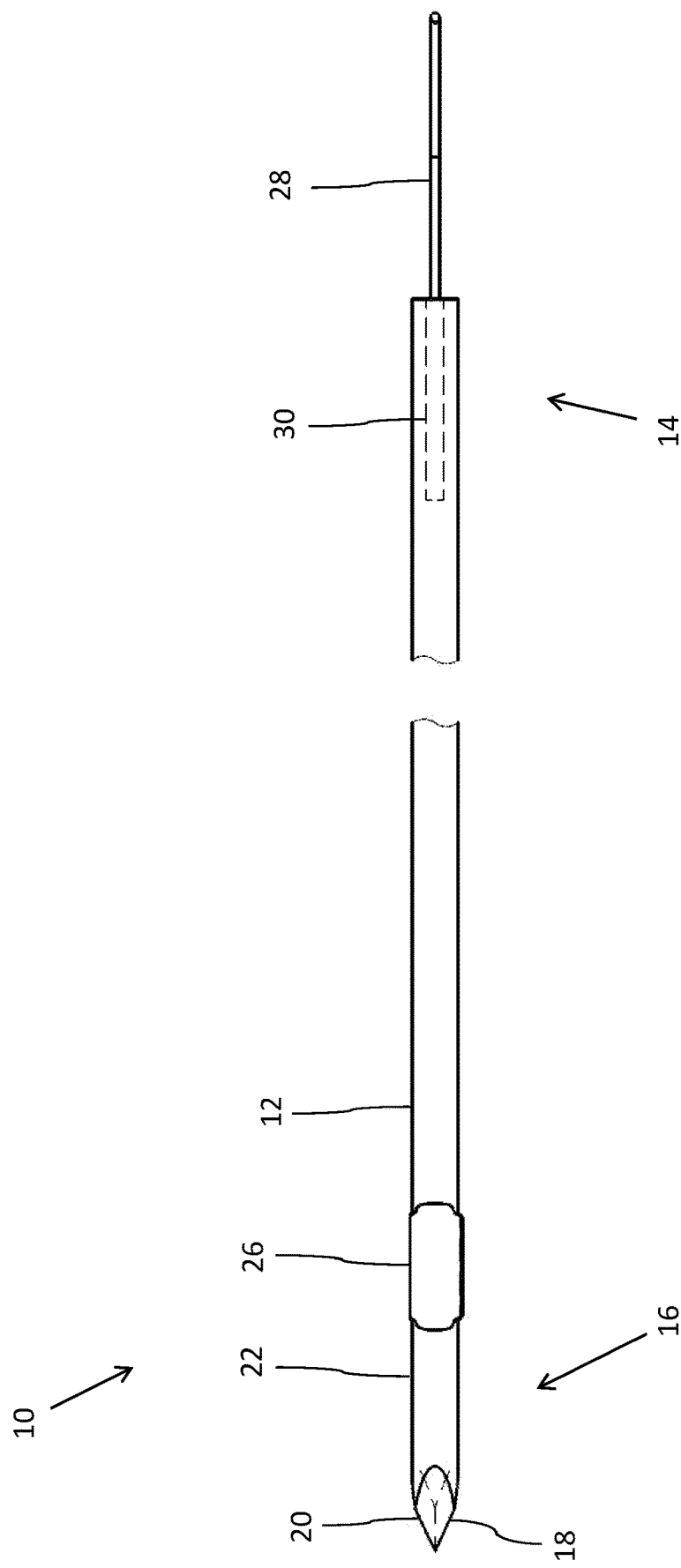
FIG. 1B is a top view schematic representation of a suture passing drill, according to an embodiment.

Referring now to the figures, wherein like reference numerals refer to like parts throughout, FIGS. 1A and 1B show side and top views schematic representations of a suture passing drill 10, according to an embodiment. The suture passing drill 10 comprises a proximal end 14 and a distal end 16 with an elongated shaft 12 extending therebetween. A first portion of the elongated shaft 12 has a first diameter d1. The elongated shaft 12 can be composed of metal, such as stainless steel, for example.

The distal end 16 of the suture passing drill 10 comprises a drill tip 18. The drill tip 18 can include a leading edge 20, which extends at an angle θ relative to a surface 22 of the elongated shaft 12, creating the tapered drill tip 18. In the depicted embodiment, the angle θ at which the leading edge 20 of the drill tip 18 extends relative to the surface 22 of the elongated shaft 12 is approximately or equal to 15°. The angle θ can vary within the range of 10°-30°.

Figure 2A:
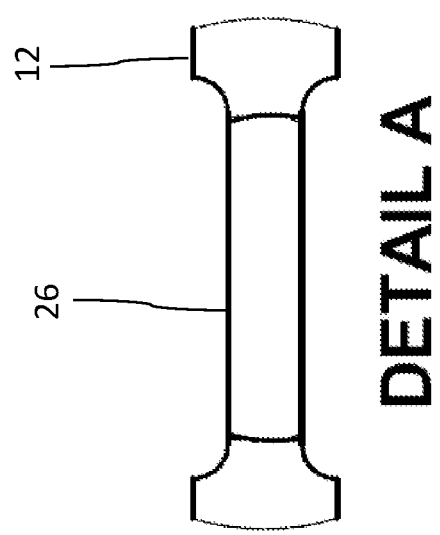
FIG. 2A is a detail view schematic representation of the narrow portion of the suture passing drill, according to an embodiment.
Figure 2B:
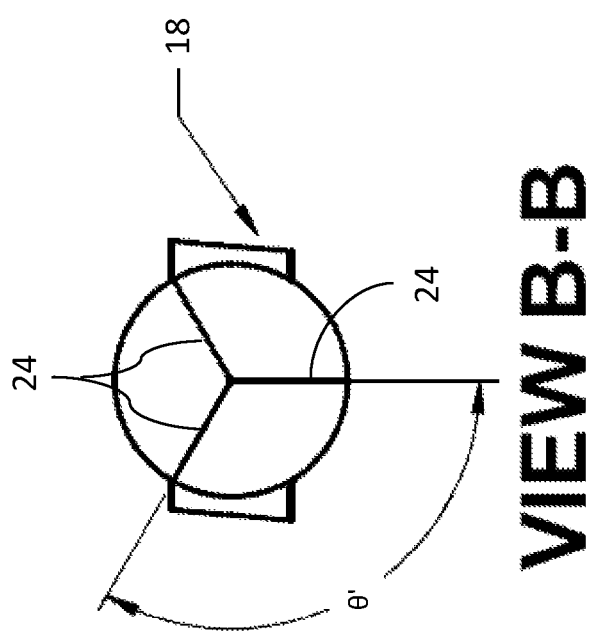
FIG. 2B is a front view schematic representation of the drill tip, according to an embodiment.

Referring briefly to FIG. 2B, there is shown a front view schematic representation of the drill tip 18. The drill tip 18 comprises one or more cutting edges 24, each having a leading edge 20 (FIGS. 1A-1B) and each extending at an angle θ' relative to each other. In the depicted embodiment, the drill tip 18 comprises three cutting edges 24. The leading edge 20 (FIGS. 1A-1B) of each of the three cutting edges 24 extends at the angle θ (FIG. 1A) relative to the surface 22 of the elongated shaft. As stated above the angle θ (FIG. 1A) is within the range of 10°-30° and in the depicted embodiment, the angle θ is the same for all three cutting edges 24. As also shown in the embodiment in FIG. 2B, the three cutting edges 24 are substantially equidistant, such that any one of the three cutting edges 24 is approximately or equal to 120° relative to any of the other cutting edges 24. Alternatively, the cutting edges 24 are not necessarily substantially equidistant, such that any one of the three cutting edges 24 is different than at least one of the other cutting edges 24. For example, the angle θ' between each of the cutting edges 24 may vary by up to 15° as long as the angles θ' between all three cutting edges 24 add up to 360°.

Turning back to FIGS. 1A and 1B, the elongated shaft 12 comprises a narrow portion 26 at the distal end 16 of the suture passing drill 10 adjacent to the drill tip 18. In other words, the narrow portion 26 is proximally located on the elongated shaft 12 relative to the drill tip 18. The narrow portion 26 has a second diameter d2, which is smaller than the first diameter d1 of the elongated shaft 12, as also shown in FIG. 2A. The narrow portion 26 can be created by any known methods, such as coining the area of the elongated shaft 12 designated for the narrow portion 26. Coining is a preferred method for creating the narrow portion 26 in the elongated shaft 12 because it prevents the need for machining the outer diameter (or surface 22) of the elongated shaft 12 proximal to the drill tip 18 in order to create a larger drill tip 18.

Still referring to FIGS. 1A and 1B, the suture passing drill 10 additionally comprises a loop 28 at its proximal end 14. The loop 28 is composed of wire, such as nitinol. In the depicted embodiment, the loop 28 is diamond-shaped. As shown in FIG. 1A, the loop 28 can comprise a width w, which, at its largest point, is larger than the first diameter d1 of the elongated shaft 12. The width w of the loop 28 can be opened or otherwise expanded because it is composed of an elastic material and it will return to the original width w if nothing is positioned through the loop 28. As also shown in the depicted embodiment, at least a portion 30 of the loop 28 is attached to or within the elongated shaft 12. The loop 28 can be attached within the elongated shaft 12 such that the loop 28 meets a minimum pullout strength of 6 lbs. In an embodiment, the portion 30 of the loop 28 within the elongated shaft 12 is twisted in order to maintain the shape of the loop 28.

As described above, the suture passing drill 10 in FIGS. 1A-1B can be used to drill and form a bone tunnel. The suture passing drill 10 can also be used to pass suture through the bone tunnel in order to create the suspension required in certain orthopedic procedures, as should be understood by a person of ordinary skill in the art in conjunction with a review of this disclosure.

Figure 3:
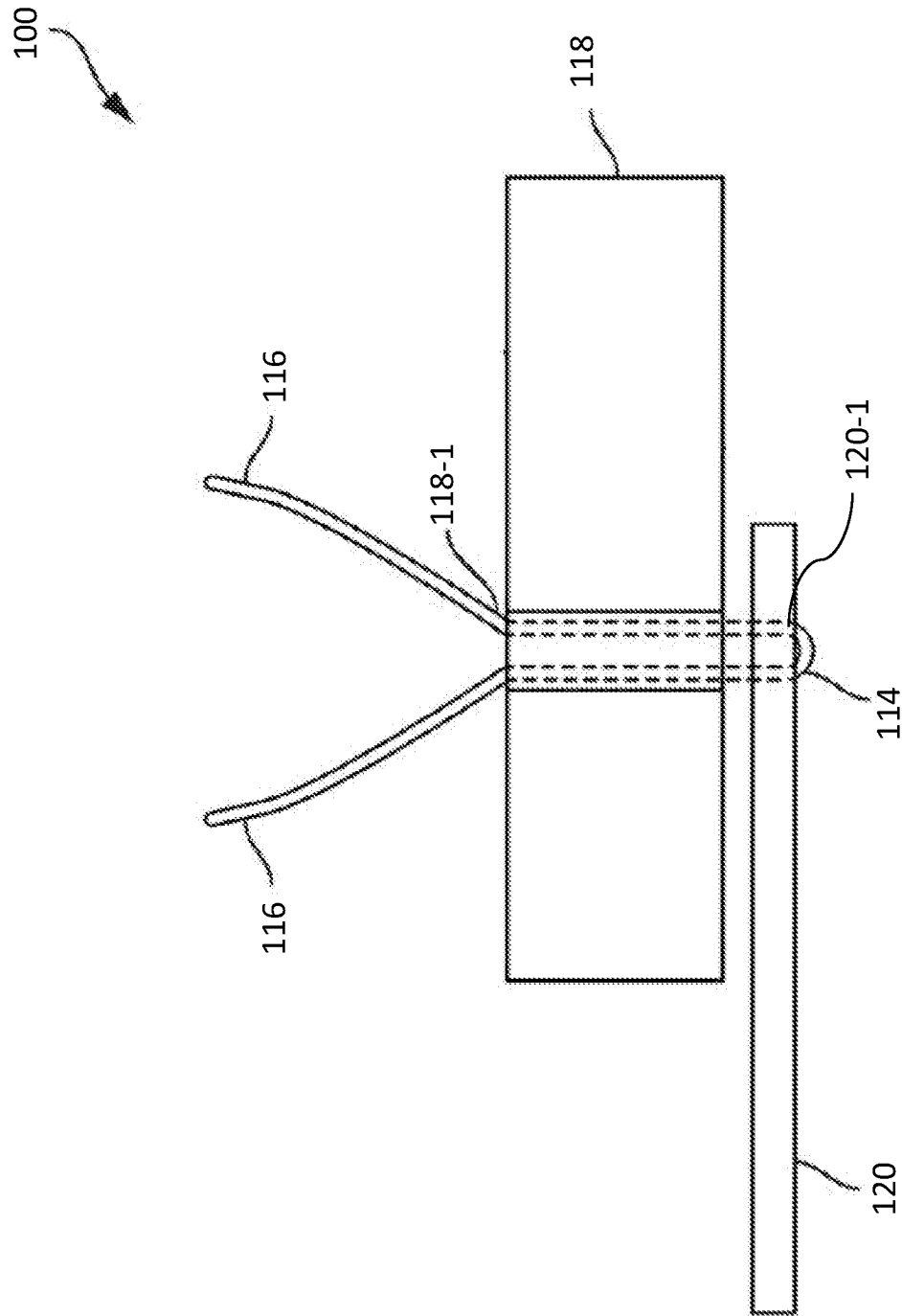
FIG. 3 is a top perspective view schematic representation of the free limbs of suture threaded in loading loops, according to an embodiment.

Turning now to FIG. 3, there is shown a side views schematic representation of a suture backstop system 100 installed by the suture passing drill 10 (FIGS. 1A-1B). The suture passing drill 10 is used to drill a single hole 118-1 through a first body 118. The first body 118 is preferably bone, but may also be soft tissue or a graft. The user may then continue to drive the suture passing drill 10 to drill a single hole 120-1 through a second body 120. The second body 120 may also be a bone, soft tissue, or a graft. As shown in FIG. 3, the second body 120 is positioned adjacent distally relative to the first body 118.

Prior to drilling the holes 118-1, 120-1 in the first and second bodies 118, 120, a length of suture 114 is attached to the loop 28 of the suture passing drill 10. Thus, after the suture passing drill 10 creates the hole 118-1 in the first body 118 and moves distally to create the hole 120-1 in the second body 120, the length of suture 14 is pulled through the hole 118-1 in the first body 118. The length of suture 114 is woven through the second body 120 and advanced back through the bone holes 120-1, 118-1 to form the partial or undeployed configuration of the suture backstop system 100 shown in FIG. 3—where the length of suture 114 is shown with two free limbs 116 extending proximally from the first body 118. The portion of the length of suture 114 (including, but not limited to both limbs 116) positioned between first body 118 and second body 120 can be considered a bridge, as discussed with respect to the suture suspension system 100 below (although, the "bridge" in this embodiment can be relatively shorter).

Figure 4:
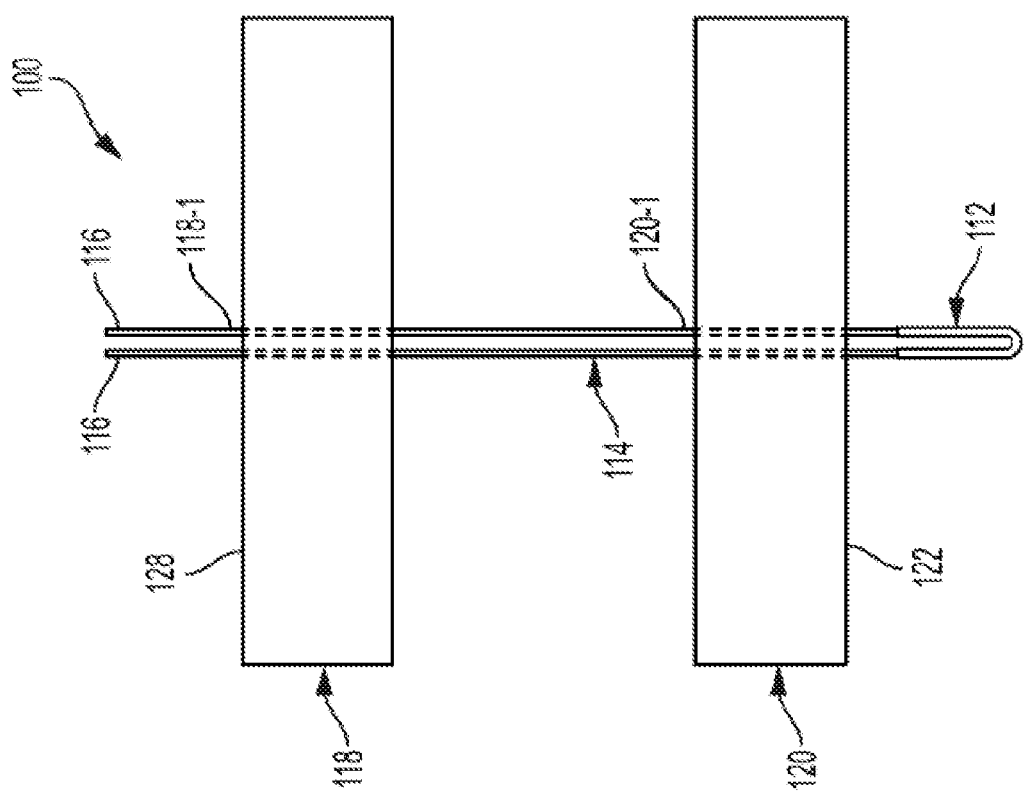
FIG. 4 is a side view schematic representation of the suture suspension system, according to an embodiment.

Referring now to FIG. 4, there is shown a side schematic view representation of the suture suspension system 100 in a partial or undeployed configuration, according to an alternative embodiment. As shown, the length of suture 114 is woven through an anchoring body 112. In the depicted embodiment, the anchoring body 112 is an all-suture button in an expanded position. In another embodiment, the anchoring body 112 can be a suspensory fixation device as described in U.S. Pat. No. 9,700,403 assigned to the assignee hereof and incorporated by reference herein in its entirety. In brief, an embodiment of the suspensory fixation device can include an elongated anchor member (which may or may not have preformed suture receiving apertures, where at least one of which can, but doesn't have to be, recessed within a surface of the elongated anchor member), and a suture threaded through at least one of the apertures. In an alternative embodiment, the anchoring body 112 can be any soft suture anchor material (as should be understood by a person of ordinary skill in the art in conjunction with a review of this disclosure). In brief, since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) along with a suture or filament portion. Another example of a "soft" all-suture anchor is the Y-Knot® device. See, e.g., U.S. Pat. No. 9,826,971. Such all-suture anchors can take advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. In the aforementioned embodiments, the suture 114 is woven through the anchoring body 112 such that two free limbs 116 of suture 114 extend from the anchoring body 112.

To utilize the suspension system 100, a length of suture 114 attached to the anchoring body 112 is threaded through the loop 28 in the suture passing drill 10 of FIG. 1A. The suture passing drill 10 is then used to create the single hole 118-1 through the first body 118 and the single hole 120-1 in the second body 120. As the suture passing drill 10 advances distally, it pulls the length of suture 114 through the bone holes 118-1, 120-1, and through an all suture button 112, and advanced back through bone holes 120-1, 118-1 to form the partial or undeployed configuration shown in FIGS. 4-5 where the length of suture 114 is shown with two free limbs 116 extending proximally from the opposite/proximal/top surface 128 of bone 118. The all-suture button 112 extends distally from the distal surface 122 of second bone 120, and a section of suture 114 forms a bridge between the first bone 118 and the second bone 120.

Figure 5:
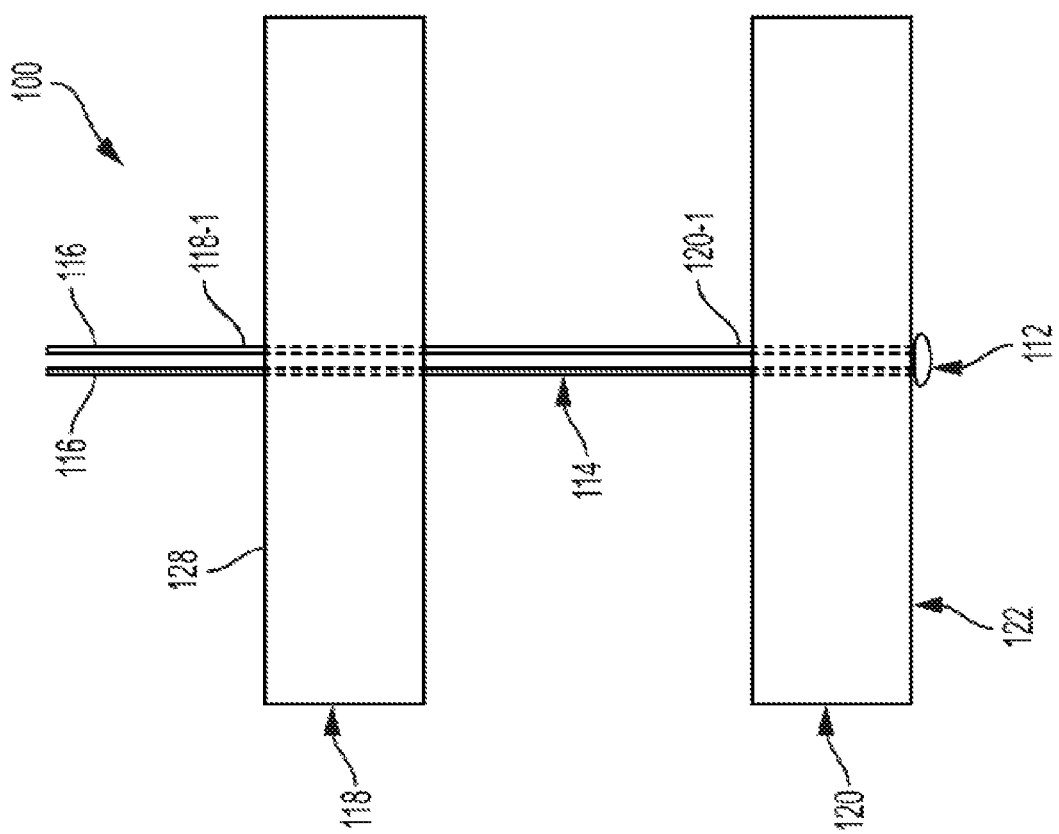
FIG. 5 is a side view schematic representation of the suture suspension system with the all-suture button in a compressed position, according to an embodiment.

As depicted in FIG. 5, the free limbs 116 of the suture 114 are pulled proximally from the first bone 118 to set the all-suture button 112 against the distal surface 122 of the second bone 120. As the suture 114 is pulled proximally, the all-suture button 112 moves from the expanded position (in FIG. 4) to a compressed position (in FIG. 5). In the compressed position, the all-suture button 112 covers a surface area on the distal side 122 of the second bone 120 larger than the diameter of the bone hole 120-1 in the second bone 120. Once the all-suture button 112 is in the compressed position, tension in the suture 114 can be used to create a suspension configuration between the first bone 118 and the second bone 120 by deploying a backstop from an expanded position to a compressed position.

Figure 6:
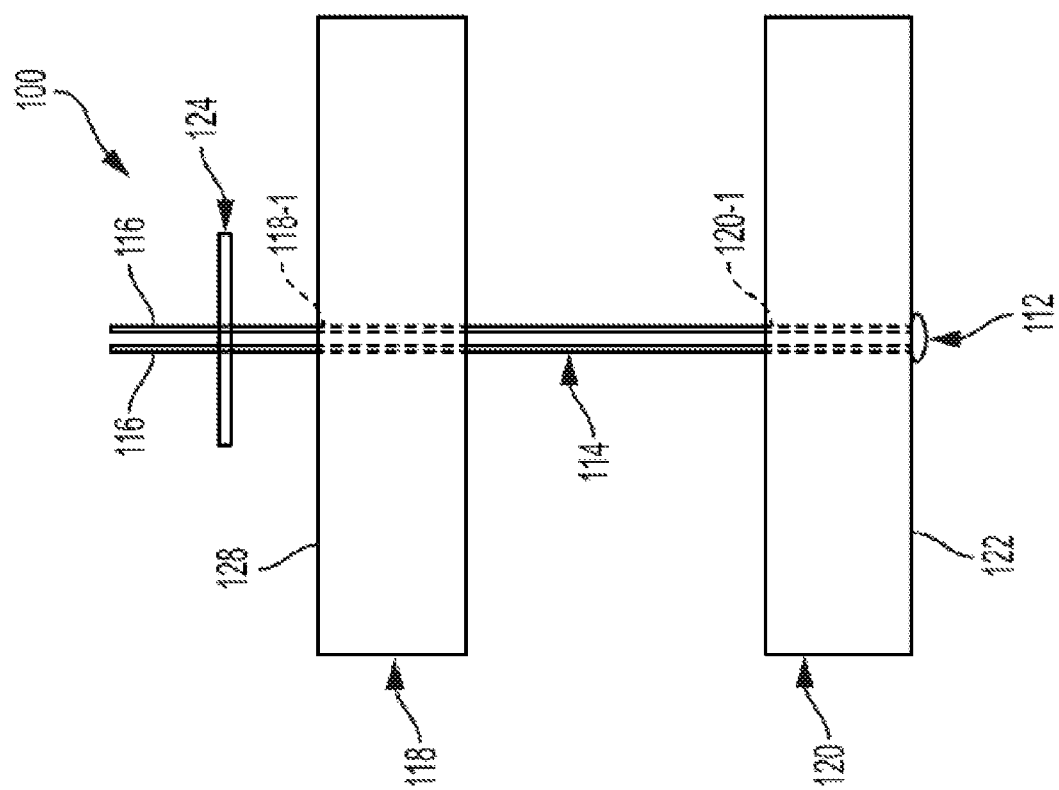
FIG. 6 is a side view schematic representation of the suture suspension system with the all-suture button in the compressed position and the all-suture backstop in the expanded position, according to an embodiment.

Turning now to FIG. 6, a backstop 124 is shown being moved distally along the suture 114 until it is against the proximal side 128 of the first bone 118. Similarly to the all-suture button 112, the backstop 124 may be a suspensory fixation device and/or comprised of any soft suture anchor material. Additionally, the backstop 124 may be comprised of radiopaque fiber so that the backstop 124 can be seen in x-ray photographs. A purpose of using an all-suture anchor backstop 124 and the all-suture button 112 is to minimize irritation and discomfort to the patient at the surgical site.

Once the backstop 124 is against the proximal side 128 of the first bone 118, additional tension in the free limbs 116 causes the backstop 124 to move from an expanded position to a compressed position. In the expanded position, ends of the backstop 124 are in a first direction along a longitudinal axis. When the backstop 124 moves into the compressed position, the ends of the backstop 124 rotate to a second direction different than the first direction. Other compressed positions are contemplated in which the backstop 124 covers a surface area on the proximal side 128 of the first bone 118 greater than the diameter of the bone hole. Purposes of the backstop 124 structure, configuration, positioning and related functionality is to prevent the suture 114 from pulling out from the first bone hole 118-1 and to maintain the tension in the suture 114 between the backstop 124 and the all-suture button 112.

Figure 7:
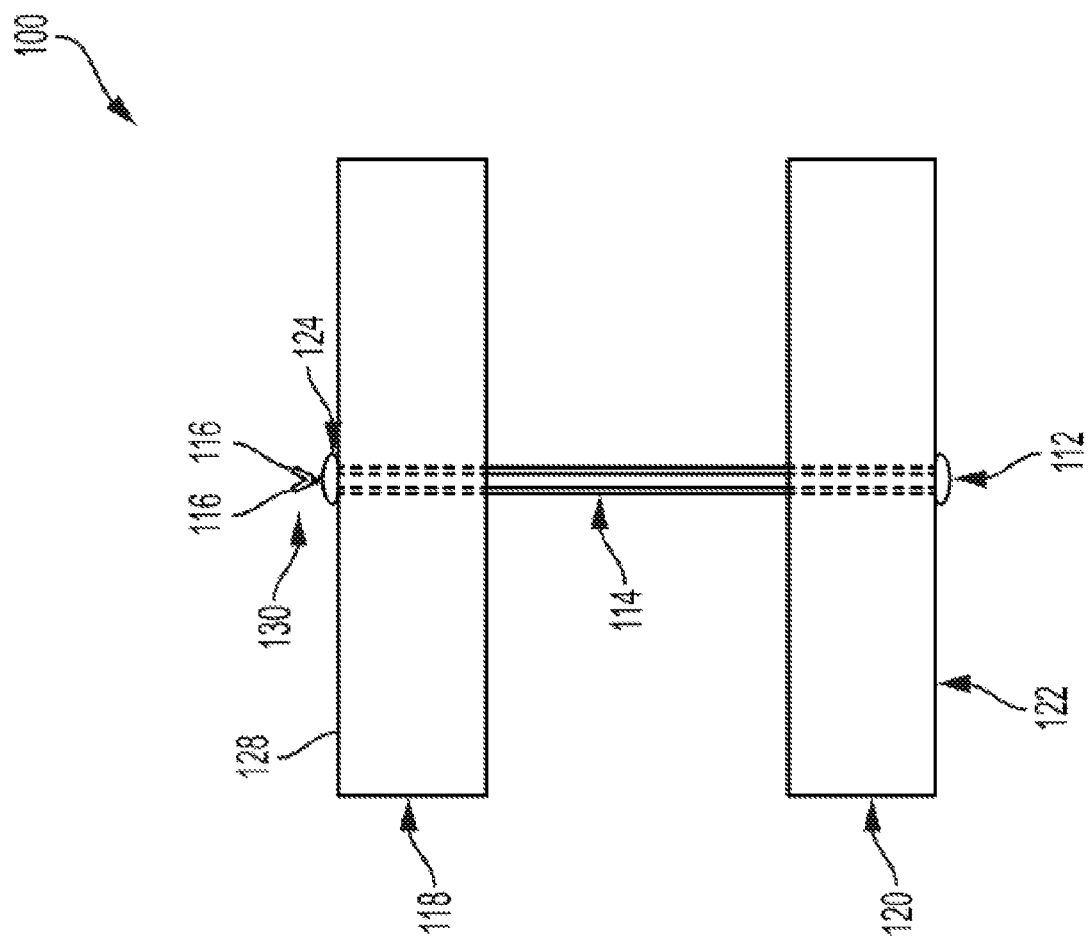
FIG. 7 is a side view schematic representation of the deployed configuration of the suture suspension system, according to an embodiment.

Turning now to FIG. 7, there is shown a side schematic view of a knot 130 formed in the free limbs 116 of suture 114 proximally over the backstop 124, i.e., the deployed configuration of the suture suspension system 100. Tying the knot 130 in the free limbs 116 secures the backstop 124 in the compressed and deployed position. Excess portions of the free limbs 116 of suture 114 that extend from the knot 130 can be trimmed and removed to decrease the potential for irritation and discomfort.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed.

Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture passing drill, comprising:
    a proximal end and a distal end with an elongated shaft extending therebetween, the elongated shaft having a first portion and a second portion with a first diameter and a first shape;
    a wire loop extending from the proximal end of the elongated shaft;
    a drill tip at the distal end of the elongated shaft;
    a narrow portion on the elongated shaft having a second diameter and a second shape, and extending between the first portion and the second portion of the elongated shaft, wherein the first portion extends with the first diameter proximally from the narrow portion to a most proximal end of the elongated shaft and includes the first diameter and the first shape, the narrow portion being positioned closer to the distal end than to the proximal end; and
    wherein the second diameter is smaller than the first diameter, and the first shape is different than the second shape.

2. The suture passing drill of claim 1, wherein the drill tip comprises a leading edge extending at an angle from a surface of the elongated shaft.

3. The suture passing drill of claim 2, wherein the leading edge extends about 25° from the surface of the elongated shaft.

4. The suture passing drill of claim 1, wherein the drill tip comprises three cutting edges.

5. The suture passing drill of claim 4, wherein one of the three cutting edges extends 120° relative to another of the three cutting edges.

6. The suture passing drill of claim 1, wherein the narrow portion is coined into the elongated shaft.

7. The suture passing drill of claim 1, wherein the wire loop comprises a third diameter at a largest opening position of the wire loop, which is larger than the first diameter.

8. The suture passing drill of claim 1, wherein the wire loop is composed of nitinol.

9. The suture passing drill of claim 1, wherein the elongated shaft is composed of stainless steel.

10. The suture passing drill of claim 1, further comprising a length of suture attached to the wire loop.

11. The suture passing drill of claim 10, wherein the length of suture is woven through an anchoring body.

12. The suture passing drill of claim 11, wherein the anchoring body is an all-suture button.

13. A method for tensioning a first body relative to a second body, comprising the steps of:
    providing a suture passing drill comprising a proximal end and a distal end with an elongated shaft extending therebetween, the elongated shaft having a first portion and a second portion with a first diameter and a first shape, a wire loop extending from the proximal end of the elongated shaft, a drill tip at the distal end of the elongated shaft, a narrow portion on the elongated shaft having a second diameter and a second shape, and extending between the first portion and the second portion of the elongated shaft, wherein the first portion extends with the first diameter proximally from the narrow portion to a most proximal end of the elongated shaft and includes the first diameter and the first shape, the narrow portion being positioned closer to the distal end than to the proximal end, wherein the second diameter is smaller than the first diameter, and the first shape is different than the second shape;
    attaching a length of suture to the wire loop;
    drilling a first hole in a first body with the drill tip of the suture passing drill;
    drilling a second hole in a second body with the drill tip of the suture passing drill; and
    pulling the suture passing drill through the second hole such that the length of suture extends between the first body and the second body.

14. The method of claim 13, further comprising the step of passing the length of suture through an anchoring body.

15. The method of claim 14, wherein the anchoring body is an all-suture button.

16. The method of claim 14, wherein the anchoring body is positioned on a distal surface of the second body.

17. The method of claim 16, wherein free limbs of the length of suture extend from a proximal surface of the first body.

18. The method of claim 17, further comprising the step of passing the free limbs through a flexible backstop.

19. The method of claim 13, further comprising the step of tensioning the length of suture between the first body and the second body.

20. The method of claim 13, wherein the first body and second body are bones.

* * * * *